July 2, 1957 M. J. MURRAY Plant Pat. 1,613

MINT PLANT

Filed Aug. 31, 1955

INVENTOR.
MERRITT J. MURRAY
BY Lindley E. Mills

United States Patent Office

Plant Pat. 1,613
Patented July 2, 1957

1,613

MINT PLANT

Merritt J. Murray, Kalamazoo, Mich., assignor to A. M. Todd Company, Kalamazoo, Mich., a corporation of Michigan Application August 31, 1955, Serial No. 531,855

1 Claim. (Cl. 47—59)

This invention relates to a new and distinct variety of mint plant which was initially produced by hybridization of tetraploid *Mentha arvensis* L. *piperascens* Briq. with a first generation hybrid of tetraploid *Mentha sylvestris* L. (*Mentha longifolia* (L.) Huds.) by *Mentha crispa* L. (*Mentha spicata* L. var. *crispata*) and thereafter asexually reproduced from stolons at nurseries near Kalamazoo, Michigan, and in central Washington.

The new variety is characterized by its erect habit, by its stiff coarse stems, by its very leafy character and its exceeding vigor. It generally grows to a height of about three feet or somewhat more under central Washington field conditions. Its stems are quite rigid and it is much less fragile than *Mentha arvensis* L. *piperascens* Briq. It is especially characterized by the high total menthol content of its oil. The colors of the plant and flowers are not distinctive and resemble closely those of other mint varieties grown under similar conditions. It is extremely hardy under central Washington field conditions.

The leaves of the new variety are opposite and lanceolate, being broader at the base than the leaves of *Mentha arvensis* L. *piperascens* Briq. The leaves are moderately serrated, the serrations generally extending somewhat nearer to the leaf petiole than in the case of *Mentha arvensis* L. *piperascens* Briq. The leaves, stems and flowers are almost non-hairy, only a very few sparse hairs generally being observed, principally on the under side of the leaf veins. The stems are essentially smooth.

The flowers are borne in axially globular clusters, the leaves on the flower spikes being smaller than the leaves on the non-flowering portions of the stem and decreasing in size to very small leaves resembling small spikes at the ends of the flower spikes.

The new variety is highly resistant to powdery mildew, *Erysiphe cichoraccarum* D. C., and to leaf spot diseases, including *Cephalosporium sp.*, which attack *Mentha arvensis* L. *piperascens* Briq.

The resistance of the new variety to these organisms was demonstrated in field plots on upland soil near Mentha, Michigan. Disease conditions were accentuated by interplantings of *M. arvensis* L. *piperascens* Briq. and of *M. citrata* Ehrh., *M. piperita* L., *M. cardiaca* (Gerarde or Baker?), *M. spicata* L. and other susceptible wild species as well as of a number of susceptible hybrid varieties under test. Mildew conditions were accentuated by shaking and spreading greenhouse grown *M. arvensis* L. *piperascens* Briq. heavily infested with powdery mildew over the plot. A similar second plot was planted the next year adjacent the first with stock taken from the first plot. The first year's plot was left unplowed, the plants in it being permitted to grow undisturbed the second year to furnish additional continuing inoculation of the second plot.

Susceptible varieties in both plots, including *M. arvensis* L. *piperascens* Briq. were heavily infested with mildew and leaf spot diseases, including *Cephalosporium sp.* The new variety was not attacked significantly in either plot by powdery mildew or leaf spot diseases.

Similar test procedures were carried out near Toppenish, Washington, under conditions of both overhead and ditch irrigation with comparable results.

The new variety is particularly remarkable for the high content of total menthol in its oil as compared with *Mentha piperita* L., the usual American commercial variety of mint. The oil of the new variety generally contains from about 75 to about 78 percent of total menthol as determined by the method for total menthol content given in the United States Pharmacopoeia No. 14.

In the drawings, which are photographic illustrations of the new variety:

Figure 2:
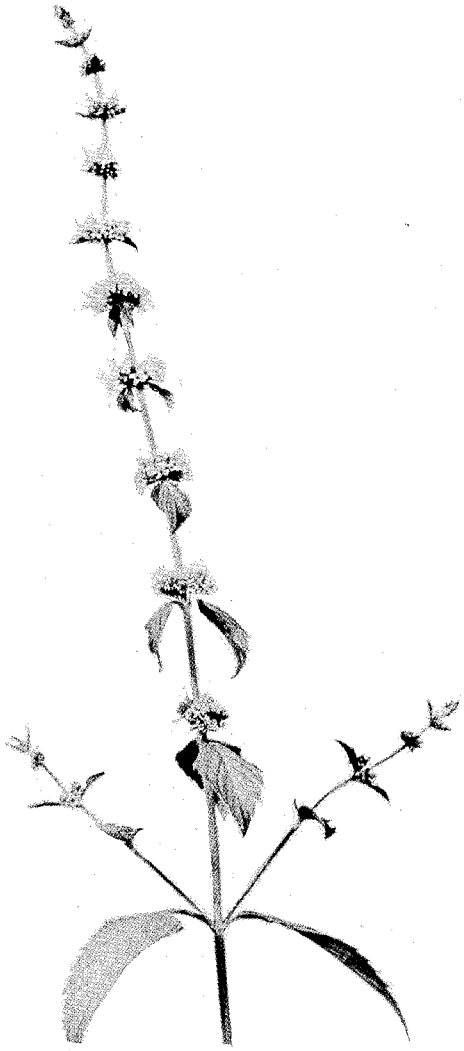
Figure 2 is an enlarged view of a flower stem illustrating the habit of the new variety of bearing its flowers in axillary clusters.
Figure 1:
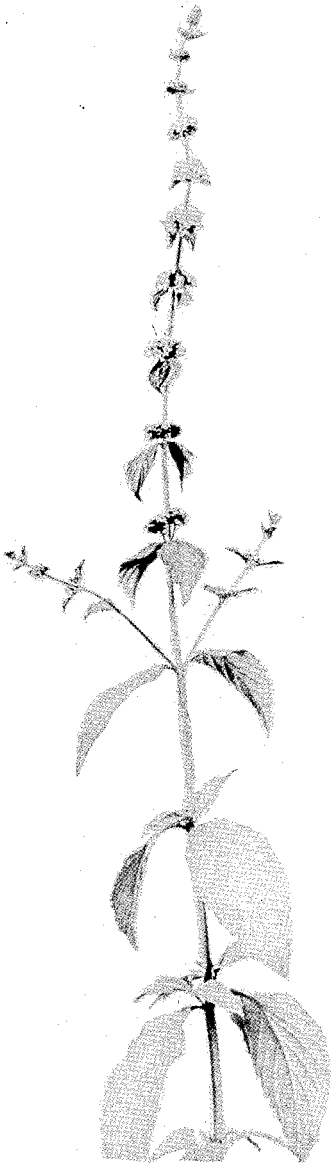
Figure 1 is a side view of a branch of the new variety.

The hybridization leading to the new variety was carried out in the summer of 1952 in southern Michigan. The seed resulting from the hybridization was planted and grown in the spring and summer of 1953. The new variety was selected from among a large number of other hybrids as being of commercial value because of the toughness of its stems, its high total menthol content and its immunity to disease, and was first asexually reproduced in central Washington in the spring of 1954. It has been grown by asexual reproduction in central Washington since that time. It has consistently exhibited its hardy characteristics, its lack of fragility and the high total menthol content of its oil referred to previously.

I claim:

A new and distinct variety of mint plant substantially as described, characterized particularly by its coarse stems and non-fragile nature, its exceptionally leafy character and by the high total menthol content of its oil as compared with *Mentha piperita* L.

No references cited.